United States Patent
Dang et al.

(10) Patent No.: US 11,465,107 B2
(45) Date of Patent: Oct. 11, 2022

(54) PROCESS FOR PRODUCING A NANO OMEGA-3 MICROEMULSION SYSTEM

(71) Applicant: Hong Ngoc Thi Dang, Ho Chi Minh (VN)

(72) Inventors: Hong Ngoc Thi Dang, Ho Chi Minh (VN); Nam Hai Lai, Ho Chi Minh (VN)

( * ) Notice: Subject to any disclaimer, the term of this patent is extended or adjusted under 35 U.S.C. 154(b) by 19 days.

(21) Appl. No.: 16/531,818

(22) Filed: Aug. 5, 2019

(65) Prior Publication Data

US 2019/0351378 A1 Nov. 21, 2019

(51) Int. Cl.
| | |
|---|---|
| *B01F 23/411* | (2022.01) |
| *B01F 23/40* | (2022.01) |
| *C09K 23/00* | (2022.01) |
| *B01F 23/41* | (2022.01) |
| *B01F 23/80* | (2022.01) |
| *A61K 9/107* | (2006.01) |

(52) U.S. Cl.
CPC ............ *B01F 23/411* (2022.01); *B01F 23/49* (2022.01); *B01F 23/808* (2022.01); *C09K 23/00* (2022.01); *A61K 9/1075* (2013.01); *B01F 23/4143* (2022.01); *B01F 23/4146* (2022.01); *B01F 23/48* (2022.01)

(58) Field of Classification Search
CPC .......................................... B01F 3/0811–0815
See application file for complete search history.

(56) References Cited

U.S. PATENT DOCUMENTS

| | | | | |
|---|---|---|---|---|
| 4,867,986 A * | 9/1989 | Desai | ........................ | A61K 9/50 424/464 |
| 6,234,464 B1 * | 5/2001 | Krumbholz | .............. | B01J 13/06 264/4.32 |
| 6,284,268 B1 * | 9/2001 | Mishra | ................. | A61K 9/4858 424/455 |
| 8,158,134 B1 * | 4/2012 | Supersaxo | ........... | A61K 9/1075 424/400 |
| 2007/0087104 A1 * | 4/2007 | Chanamai | .............. | A23D 7/003 426/602 |
| 2007/0148194 A1 * | 6/2007 | Amiji | .................... | A61K 9/1075 424/400 |
| 2008/0199589 A1 * | 8/2008 | Patist | ....................... | A23L 33/12 426/602 |
| 2008/0274195 A1 * | 11/2008 | Nicolosi | .............. | A61K 9/1075 424/489 |
| 2009/0297491 A1 * | 12/2009 | Bromley | .............. | A61K 36/286 424/94.1 |
| 2011/0045050 A1 * | 2/2011 | Elbayoumi | .......... | A61K 9/1075 424/423 |
| 2012/0251596 A1 * | 10/2012 | Fratter | ................. | B01F 17/0092 424/400 |
| 2014/0105829 A1 * | 4/2014 | Ganta | ................. | A61K 49/1806 424/9.364 |
| 2015/0051298 A1 * | 2/2015 | McClements | .......... | A01N 25/04 514/731 |
| 2017/0112764 A1 * | 4/2017 | Wu | ........................ | A61K 8/062 |

FOREIGN PATENT DOCUMENTS

WO WO-9956727 A2 * 11/1999 ........... A61K 9/1075

* cited by examiner

*Primary Examiner* — Stephen E Rieth
(74) *Attorney, Agent, or Firm* — BN IP-Consulting LLC; Binh-An Nguyen

(57) ABSTRACT

The present invention relates to a process of producing a nano Omega-3 microemulsion system includes: (i) preparing a dispersal phase by heating Omega-3; (ii) preparing a carrier by heating a liquid PEG (polyethylene glycol); (iii) adding the carrier to the dispersal phase; (iv) emulsifying as follows: when the temperature arrives at 60° C., adding ACRYSOL K-140 to the mixture of the carrier and dispersal phase in step (iii), continuing to stir at a speed of 500 to 700 rpm, at a temperature of 60 to 80° C., in vacuum, for 3 to 5 hours, controlling the quality of resulting product by dissolving into water and measuring the transparency, the reaction is quenched, the temperature is decreased slowly until it is in the range of 40 to 60° C.; emulsifying for the entire mixture for 30 minutes; (v) filtrating the product by injecting through nanofilter system before filling-packaging.

1 Claim, 1 Drawing Sheet

PROCESS FOR PRODUCING A NANO OMEGA-3 MICROEMULSION SYSTEM

TECHNICAL FIELD

The present invention relates to a process for producing a nano Omega-3 microemulsion system.

BACKGROUND OF THE PRESENT INVENTION

Omega-3 is a group of unsaturated fatty acids with multiple double bonds, and the double bond is most needed at the 3rd carbon position, which our bodies cannot synthesize themselves, must be supplemented through food. Omega-3 fatty acids are abundant in cold and deep-sea fish such as tuna, salmon, mackerel, etc.

The unsaturated fatty acids with multiple double bonds such as linoleic acid (Cis-9,12-Octadecadienoic acid, C18:2) and alpha linolenic acid (Cis-9,12,15-Octadecatrienoic acid, C18:3) are also classified as Omega-6 and Omega-3 fatty acids, are very important in animal nutrition, especially in humans. Omega-3 fatty acids have important function in the formation of nerve and eye tissue, responding to the stable functioning of the cardiovascular system and regulating the activity of the immune system (Neuringer et al., 1988; Levinson et al., 1990). Omega-3 fatty acids are used in many functional foods to meet the nutritional needs of human biological system. However, it is unstable during processing and storage, insoluble in water, with low bioavailability if used normally, is easily denatured. Nano emulsions can be used as distribution systems to increase stability (Karthik, P. Et al., 2016). The need for the process of producing microemulsions system with micelles of size less than 100 nm, uniform, better solubility in water and still retain the structure and activity of Omega-3 in the nanoprocessing. Nano emulsions are convenient for absorption in the intestine, it is easily dispersed in liquid medium. The Omega-3 nano emulsion system helps increase absorption, especially for cancer patients, who have problem swallowing solid dosage forms. Encapsulated in nanoparticles and formulas such as O/W systems (oil/water systems, droplets dispersed in water) minimize the fishy and unwanted taste of the Omega-3.

Anitha Krishnan Nair et al. in US Patent Publication No. 2011/0229532 A1 provided a process for producing a microemulsion system of compounds belonging to an oleophylic polyphenol group by using ultrasonic with non-ionic surfactant and one non-ionic solvent to enhance the water solubility. In particular, the invention relates to a nanoprocessing of curcumin and its derivatives which is not applied for other agents.

Inventor et al. in China Patent Publication No. CN106723052A provided a method of preparing nano linseed oil emulsion rich in Omega-3. The above method produces micelles of large size about 500 nm.

The mentioned-above processes provide micelles with dimensions greater than 100 nm, then the water-soluble effectiveness is still not high. Processes for generating micelles of curcumin and its derivatives cannot be applied for Omega-3 because those will lose the activity of Omega-3.

Therefore, there is a demand of a process for producing a microemulsion system having micelles with dimensions smaller than 100 nm, uniformity, better water-solubility while retaining the structure, activity of Omega-3 in nanoprocessing.

SUMMARY OF THE PRESENT INVENTION

An object of the present invention is to provide a process for producing a nano Omega-3 microemulsion system to produce particles having dimensions smaller than 100 nm, uniformity, ability to dissolve in water while the activity and structure is retained to help increase utility effects of Omega-3 active agents, in particular, increase the ability of absorption and increase the bioavailability.

To achieve the above object, the process for producing a nano Omega-3 microemulsion system of the present invention includes:

(i) preparing a dispersal phase by heating Omega-3 to a temperature from 40 to 60° C.;

(ii) preparing a carrier by heating a liquid PEG (polyethylene glycol) to a temperature ranging from 40 to 60° C., stirring evenly;

(iii) adding the carrier to the dispersal phase in a ratio by mass of 3:1, continuing to keep the said dispersal phase at a temperature ranging from 40 to 60° C., stirring at a speed of 400 to 800 rpm in vacuum;

(iv) emulsifying as follows: when the temperature arrives at 60° C., adding ACRYSOL K-140 to the mixture of the carrier and dispersal phase in step (iii) in a ratio by mass of 6:4, continuing to stir at a speed of 500 to 700 rpm, at a temperature of 60 to 80° C., in vacuum, the reaction temperature is kept at a temperature ranging from 60 to 80° C. for 3 to 5 hours, controlling the quality of resulting product by dissolving into water and measuring the transparency, if it fails then continuing heating and measuring this transparency every 30 minutes until it is observed to be transparent, the reaction is quenched, the temperature is decreased slowly until it is in the range of 40 to 60° C.; emulsifying in a emulsifying device for the entire mixture for 30 minutes, at a stirring speed of 400 to 800 rpm;

(v) filtrating the product by injecting through nanofilter system before filling-packaging.

DETAILED DESCRIPTION OF THE PRESENT INVENTION

Figure 1:
FIG. 1 shows a picture comparing the water-dispersing ability between a known Omega-3 (A) and the nano Omega-3 obtained by the process of the invention (B).

The process for producing a nano Omega-3 microemulsion system of the present invention is performed as follows:

(i) First step: preparing a dispersal phase by heating Omega-3 to a temperature from 40 to 60° C. The heating facilitates this dispersal phase being able to combine better with PEG carrier. The use of stirring and heating generates Omega-3 dispersing better, when the inventors carried out the experiments under various stirring conditions and temperatures, it was shown that at a stirring speed of 300-500 rpm and simultaneously heating at a temperature ranging from 40 to 60° C., the dispersal phase of Omega-3 was better and the combination with PEG carrier was better.

(ii) Second step: preparing a carrier by heating a liquid PEG (polyethylene glycol) accounted for 40 to 60% mass of the mixture of PEG and water to a temperature from 40 to 60° C., stirring evenly.

When being used, Omega-3 easily denatured to light, temperature, often damaged in the digestive tract, a portion is absorbed into the blood, most of the rest is eliminated. Thus, it needs a process for producing micelles containing Omega-3 active agent that have small size with bio-coating, stable structure, inadherence and high solubility. Because the microemulsion system of the present invention is employed in food and pharmaceutical industries, the agent selected to use must have high safety, non-toxicity and less side effects.

Many studies have shown that transporting processes of drugs may be improved the effectiveness by vehicle systems derived from kinds of polymers: natural hydrophylic polymer such as proteins (gelatine, albumine), polysaccharide (alginate, dextrane, chitosane), synthetic hydrophobic polymer such as polyester (poly (ε-capprolactone), polylactic acid, polylactic-co-glycolic acid. Polymer carriers with relatively high drug loadings can confer many conveniences in pharmacokinetics, namely drugs are kept stably, which can be administered to treat for a long time by the slowly-released process of drugs according to the decomposition of polymer, the biological distribution of drugs, the targeting, the penetration through cell membranes, etc., that can be driven by physicochemical properties of polymer.

(iii) Third step: adding the carrier to the dispersal phase (in a ratio of 3:1), continuing to keep the said dispersal phase at a temperature ranging from 40 to 60° C., stirring at a speed of 400 to 800 rpm.

(iv) Forth step: emulsifying as follows: emulsifying as follows: when the temperature arrives at 60° C., adding ACRYSOL K-140 to the mixture of the carrier and dispersal phase in step (iii) in a ratio by mass of 6:4, continuing to stir at a speed of 500 to 700 rpm, at a temperature of 60 to 80° C., in vacuum, the reaction temperature is kept at a temperature ranging from 60 to 80° C. for 3 to 5 hours, controlling the quality of resulting product by dissolving into water and measuring the transparency, if it fails then continuing heating and measuring this transparency every 30 minutes until it is observed to be transparent, the reaction is quenched, the temperature is decreased slowly until it is in the range of 40 to 60° C.

By theoretical and experimental studies, the inventors found that to produce nano Omega-3 with good water solubility, the emulsion system will be in the form of oil-in-water emulsion. Selecting emulsifier to enhance the durability of the microemulsion system was based on properties of this microemulsion system (in the form of oil-in-water microemulsion system, in the form of water-in-oil microemulsion system, etc.). Thus, the inventors selected ACRYSOL K-140, also known as PEG-40 hydrogenated castor oil, as an emulsifier, because ACRYSOL K-140 is a hydrophylic, non-toxic and highly safe agent. The inventors had to carry out so many studies to determine ratios of PEG:ACRYSOL K-140 is 6:4 to generate sustainable polymer chains.

As the emulsifier ACRYSOL K-140 is a molecule with 2 distinct portions, an oleophylic portion and a hydrophylic portion, it is capable of forming linkages with Omega-3 and carrier mixture. The oleophylic portion of ACRYSOL K-140 forms a linkage with the Omega-3 and the hydrophylic portion of ACRYSOL K-140 forms a linkage with the hydrophylic portion of the mixture of PEG carrier, then create nano Omega-3 micelles and protect Omega-3 activity well with this structure.

Thus, generating a nano Omega-3 microemulsion system by simultaneously stirring at a speed of 400 to 600 rpm in vacuum, the reaction temperature is kept at a temperature ranging from 60 to 80° C. for 3 to 5 hours, then emulsifying in a emulsifying device for the entire mixture for 30 minutes, at a stirring speed of 400 to 800 rpm.

The microemulsion system obtained by the process of the present invention has pH of 7 to 7.4. With these pH value, micelles exist stably because in this neutral environment the linkage between the resveratrol and the carrier material is kept in dispersing process, while the microemulsion system has pH<7 then this linkage weakens resulting the damage of nano resveratrol particles in the digestive tract.

The nano Omega-3 microemulsion system obtained by the process of the present invention having a hydrophilic lipophilic balance HLB, ranging from 13 to 18, is a water-emulsion emulsion. The microemulsion system has micelles containing hydrophylic Omega-3, are inadherent, with particle sizes ranging stably from 30 to 80 nm, then it can easily penetrate via cell membranes to develop the effectiveness and increase the solubility of Omega-3 in water, thereby enhance the bioavailability of the agent.

(v) Fifth step: filtrating the product by injecting through nanofilter system before filling-packaging to remove excessive amounts of agents and ensure the uniformity, the stability of solution.

EXAMPLES

Example: Production of 100 ml of Nano Omega-3 Microemulsion System

Preparing a dispersion phase by stirring 10 g Omega-3 at speed of 400 rpm, simultaneously heated to a temperature of 50° C.

Preparing a carrier: 30 ml of PEG was heated to 60° C. 30 ml of the carrier was added to the above-prepared dispersal phase, this dispersal phase continued to be heating to 60° C., stirred at a speed of 600 rpm, in vacuum. A homogeneous mixture was prepared by mixing the dispersal phase, a mixture of PEG carrier and emulsifier ACRYSOL K-140 (60 ml) in an emulsifying equipment LSP-500 with a frequency of 20 KHz at a stirring speed of 600 rpm, at 80° C., continued to be stirring at a speed of 600 rpm for 4 hours, in vacuum. Controlling the quality of resulting product by dissolving into water and measuring the transparency, if it fails then continuing heating and measuring this transparency every 30 minutes until it is observed to be transparent, the reaction is quenched, the temperature is decreased slowly until it was 50° C. Then at a temperature of 50° C. emulsifying at a stirring speed of 500 rpm, for 30 minutes.

Before filling, the products were injected via nanofilter system for the purpose of removing the excessive amounts of Omega-3 which did not form micelles, gave 100 ml of nano Omega-3 microemulsion system which dispersed in water well.

By UV-vis spectrophotometry method, the inventors found that positions of peaks of material Omega-3 and the nano Omega-3 microemulsion system fitted completely. This showed that the microemulsion system obtained by the process of the present invention retained the structure, activity of Omega-3 in nanoprocessing. UV-vis spectrophotometry method were used to quantify the concentration of Omega-3 in the microemulsion system. The results showed that the concentration of Omega-3 in the nano Omega-3 microemulsion system were in the range of 8 to 10%.

Figure 2:
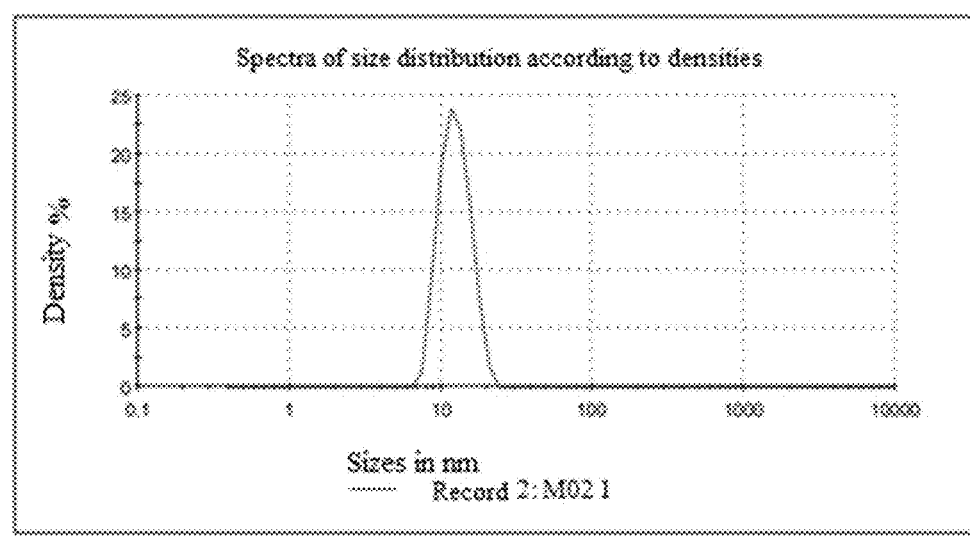
FIG. 2 shows a picture of spectra measuring by TEM the sizes of nano Omega-3 particles obtained by the process of the invention.

Measuring sizes of nano Omega-3 particles by a scanning electron microscopy TEM (Transmission Electron Microscopy) shown in FIG. 2 demonstrated that particle sizes fluctuating from 10 to 50 nm accounted for almost 100% in solution.

Particle sizes measured by DLS: particles suspending in a fluid continued undergoing random motions, and the particle sizes directly affected on their speeds. Small particles moved faster than bigger ones. In DLS, lights went through samples, and scattering lights were detected and recorded in a certain angle.

Zeta potential or kinetic potential: the potential between a dispersal phase and a dispersing media.

| Sizes (nm, according to TEM) | Sizes (nm, according to DLS) | Zeta potential (mV) | Stability (months) | Water solubility |
|---|---|---|---|---|
| 10-50 | 10-50 | −40 | >12 | Well-water solubility, after solubilized in water, the system stabilized >7 days |

The above results showed that using PEG carrier with ACRYSOL K-140 gave a microemulsion system with micelles having small dimensions (from 10 to 50 nm), high stability (>12 months), well-water solubility and after dissolved in water, the system stabilized >7 days.

With the reference to FIG. 1, it shows a picture comparing the water-dispersing ability between a known omega-3 and the nano Omega-3 obtained by the process of the present invention, in which bottle A showed the known water-dispersed Omega-3, bottle B showed the water-dispersed nano Omega-3 obtained by the process of the present invention. The nano Omega-3 obtained by the process of the present invention completely dispersed in water generated a transparent, homogeneous solution, while the known Omega-3 is insoluble in water, it floats on the surface.

With the reference to FIG. 2 showing the results of picture of spectra measuring by TEM the sizes of nano Omega-3 particles obtained by the process the present invention, it was found that the average particle size was 12.27 nm, with the density of 100%, spectrum peak 1 having the particle diameter of 12.69 nm, the width of 2.874 nm. Particles had the uniformity of sizes fluctuating from about 10 to 50 nm (FIG. 2), no other peaks appear.

Table below shows measurement data:

| | | Diameter (nm) | % density | Width (nm) |
|---|---|---|---|---|
| The average particle size (d · nm): 12.27 | Spectrum peak 1 | 12.69 | 100 | 2.874 |
| PdI: 0.077 | Spectrum peak 2 | 0.00 | 0.00 | 0.00 |
| Blocking ability: 0.939 | Spectrum peak 3 | 0.00 | 0.00 | 0.00 |
| Result of evaluation: Good | | | | |

ADVANTAGEOUS EFFECTS OF INVENTION

The process for producing a nano Omega-3 microemulsion system of the present invention succeeds in manufacturing a microemulsion system having nano Omega-3 micelles with small dimensions of about 10 to 50 nm, which is uniform and good water-soluble while retains the structure, activity of Omega-3 in nanoprocessing.

The agents used in the process for producing nano Omega-3, which disperse well in water, are highly safe, non-toxic and have less side effects, then the nano Omega-3 microemulsion system obtained by the process of the present invention has high safety when being used.

The process of the present invention is simple, easy to perform and suitable with current actual conditions in our country.

The invention claimed is:

1. A process for producing a nano Omega-3 microemulsion system includes:
   (i) preparing a dispersal phase by heating Omega-3 fatty acids to a temperature from 40 to 60° C.;
   (ii) preparing a carrier by heating a liquid PEG (polyethylene glycol) to a temperature ranging from 40 to 60° C., stirring evenly;
   (iii) adding the carrier to the dispersal phase in a ratio by mass of 3:1, continuing to keep the said dispersal phase at a temperature ranging from 40 to 60° C., stirring at a speed of 400 to 800 rpm in vacuum;
   (iv) emulsifying as follows: heating the mixture of the carrier and the dispersal phase in step (iii) to 60° C., adding PEG-40 hydrogenated castor oil as an emulsifier to the mixture in a ratio by mass of 6:4 to form a second mixture, continuing to stir at a speed of 500 to 700 rpm, at a temperature of 60 to 80° C., in vacuum, the temperature is kept at a temperature ranging from 60 to 80° C. for 3 to 5 hours;
   controlling quality of resulting product by, during the 3 to 5 hours, dissolving a sample of the second mixture into water and measuring the transparency, if not transparent then continuing heating the second mixture and measuring transparency of a sample of the second mixture dissolved in water every 30 minutes until the sample of the second mixture dissolved in water is observed to be transparent, the temperature is decreased until it is in the range of 40 to 60° C.;
   emulsifying the second mixture in a emulsifying device for 30 minutes, at a stirring speed of 400 to 800 rpm;
   (v) filtrating the product by injecting through nanofilter system.

* * * * *